United States Patent
Hlavka et al.

(10) Patent No.: US 9,867,986 B2
(45) Date of Patent: Jan. 16, 2018

(54) SYSTEM AND METHOD FOR BRONCHIAL DILATION

(71) Applicant: Holaira, Inc., Plymouth, MN (US)

(72) Inventors: Edwin J. Hlavka, Minneapolis, MN (US); Lynn Elliott, Maple Grove, MN (US)

(*) Notice: Subject to any disclaimer, the term of this patent is extended or adjusted under 35 U.S.C. 154(b) by 0 days.

(21) Appl. No.: 15/401,825

(22) Filed: Jan. 9, 2017

(65) Prior Publication Data

US 2017/0120049 A1 May 4, 2017

Related U.S. Application Data

(63) Continuation of application No. 14/841,836, filed on Sep. 1, 2015, now Pat. No. 9,539,048, which is a continuation of application No. 14/265,443, filed on Apr. 30, 2014, now Pat. No. 9,125,643, which is a continuation of application No. 13/920,801, filed on Jun. 18, 2013, now Pat. No. 8,731,672, which is a continuation of application No. 13/523,223, filed on Jun. 14, 2012, now Pat. No. 8,489,192, which is a continuation of application No. 12/372,607, filed on Feb. 17, 2009, now Pat. No. 8,483,831.

(60) Provisional application No. 61/066,026, filed on Feb. 15, 2008, provisional application No. 61/049,605, filed on May 1, 2008.

(51) Int. Cl.
| | | |
|---|---|---|
| *A61N 1/00* | (2006.01) |
| *A61N 1/36* | (2006.01) |
| *A61B 5/08* | (2006.01) |
| *A61B 18/12* | (2006.01) |
| *A61B 5/00* | (2006.01) |
| *A61B 18/00* | (2006.01) |

(52) U.S. Cl.
CPC .......... *A61N 1/3611* (2013.01); *A61B 5/0823* (2013.01); *A61B 5/4836* (2013.01); *A61B 5/686* (2013.01); *A61B 18/12* (2013.01); *A61N 1/3601* (2013.01); *A61B 2018/00434* (2013.01); *A61B 2018/00541* (2013.01)

(58) Field of Classification Search
USPC ................................ 607/2, 42, 118; 600/529
See application file for complete search history.

(56) References Cited

U.S. PATENT DOCUMENTS

| | | | |
|---|---|---|---|
| 6,411,852 B1 * | 6/2002 | Danek .................. | A61N 5/0601 128/898 |
| 7,608,275 B2 | 10/2009 | Deem et al. | |
| 7,747,324 B2 * | 6/2010 | Errico .................. | A61N 1/3601 607/42 |

(Continued)

OTHER PUBLICATIONS

Application and File history for U.S. Patent Application no. 14/265,443, filed Apr. 30, 2014. Inventors: Hlavka et al. as available on Pair at www.uspto.gov.

(Continued)

*Primary Examiner* — Nicole F Johnson
*Assistant Examiner* — Nicole F. Lavert
(74) *Attorney, Agent, or Firm* — Patterson Thuente Pedersen, P.A.

(57) ABSTRACT

A method of reducing bronchial constriction in a subject includes delivering energy to create one or more lesions on a main bronchus so as to transect pulmonary nerves sufficiently to reduce bronchial constriction in a lung of the patient distal to the main bronchus.

21 Claims, 11 Drawing Sheets

(56) References Cited

U.S. PATENT DOCUMENTS

| | | |
|---|---|---|
| 8,088,127 B2 | 1/2012 | Mayse et al. |
| 8,133,497 B2 | 3/2012 | Deem et al. |
| 8,172,827 B2 | 5/2012 | Deem et al. |
| 8,226,638 B2 | 7/2012 | Mayse et al. |
| 8,338,164 B2 | 12/2012 | Deem et al. |
| 8,483,831 B1 | 7/2013 | Hlavka et al. |
| 8,489,192 B1 | 7/2013 | Hlavka et al. |
| 8,660,647 B2 | 2/2014 | Parnis et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 | 5/2016 | Deem et al. |
| 9,398,933 B2 | 7/2016 | Mayse |
| 9,498,283 B2 | 11/2016 | Deem et al. |
| 9,539,048 B2 | 1/2017 | Hlavka et al. |
| 9,649,153 B2 | 5/2017 | Mayse et al. |
| 9,649,154 B2 | 5/2017 | Mayse et al. |
| 9,662,171 B2 | 5/2017 | Dimmer et al. |
| 9,668,809 B2 | 6/2017 | Mayse et al. |
| 9,675,412 B2 | 6/2017 | Mayse et al. |
| 2004/0226556 A1 | 11/2004 | Deem et al. |
| 2005/0065575 A1* | 3/2005 | Dobak ............... A61N 1/36007 607/45 |
| 2007/0027496 A1 | 2/2007 | Parnis et al. |
| 2007/0156185 A1* | 7/2007 | Swanson ............... A61B 1/12 607/2 |
| 2008/0051839 A1* | 2/2008 | Libbus ............... A61B 5/02028 607/2 |
| 2008/0312725 A1* | 12/2008 | Penner ............... A61N 1/0519 607/119 |
| 2011/0178569 A1 | 7/2011 | Parnis et al. |
| 2011/0257647 A1 | 10/2011 | Mayse et al. |
| 2011/0301587 A1 | 12/2011 | Deem et al. |
| 2012/0221087 A1 | 8/2012 | Parnis et al. |
| 2012/0302909 A1 | 11/2012 | Mayse et al. |
| 2012/0316552 A1 | 12/2012 | Mayse et al. |
| 2013/0310822 A1 | 11/2013 | Mayse et al. |
| 2014/0257271 A1 | 9/2014 | Mayse et al. |
| 2014/0276792 A1 | 9/2014 | Kaveckis et al. |
| 2014/0371809 A1 | 12/2014 | Parnis et al. |
| 2015/0141985 A1 | 5/2015 | Mayse et al. |
| 2016/0022351 A1 | 1/2016 | Kaveckis et al. |
| 2016/0038725 A1 | 2/2016 | Mayse et al. |
| 2016/0220851 A1 | 8/2016 | Mayse et al. |
| 2016/0278845 A1 | 9/2016 | Mayse |
| 2016/0310210 A1 | 10/2016 | Harshman et al. |
| 2017/0014571 A1 | 1/2017 | Deem et al. |
| 2017/0050008 A1 | 2/2017 | Mayse |
| 2017/0072176 A1 | 3/2017 | Deem et al. |
| 2017/0143421 A1 | 5/2017 | Mayse et al. |

OTHER PUBLICATIONS

Application and File history for U.S. Patent Application no. 14/841,836, filed Sep. 1, 2015. Inventors: Hlavka et al. as available on Pair at www.uspto.gov.

Application and File history for U.S. Patent Application no. 13/920,801, filed.

Application and File history for U.S. Patent Application no. 13/523,223, filed.

Application and File history for U.S. Patent Application no. 12/372,607, filed Feb. 17, 2009. Inventors: Hlavka et al. as available on Pair at www.uspto.gov.

* cited by examiner

SYSTEM AND METHOD FOR BRONCHIAL DILATION

RELATED APPLICATIONS

This application is a continuation of application Ser. No. 14/841,836 filed Sep. 1, 2015, which in turn is a continuation of application Ser. No. 14/265,443 filed Apr. 30, 2014, now U.S. Pat. No. 9,125,643 issued Sep. 8, 2015, which in turn is a continuation of application Ser. No. 13/920,801 filed Jun. 18, 2013, now U.S. Pat. No. 8,731,672 issued May 20, 2014, which in turn is a continuation of U.S. patent application Ser. No. 13/523,223 filed Jun. 14, 2012, now U.S. Pat. No. 8,489,192 issued Jul. 16, 2013, which in turn is a continuation of U.S. patent application Ser. No. 12/372,607 filed Feb. 17, 2009, now U.S. Pat. No. 8,483,831 issued Jul. 9, 2013, which in turn claims the benefit of U.S. Provisional Application No. 61/066,026 filed Feb. 15, 2008, and U.S. Provisional Application No. 61/049,605 filed May 1, 2008, each of which is hereby fully incorporated herein.

TECHNICAL FIELD

This document pertains generally to medical devices, and more particularly, but not by way of limitation, to systems and methods for bronchial stimulation.

BACKGROUND

Obstructive pulmonary disease, including asthma, emphysema, or chronic bronchitis, afflicts more than 25 million individuals in the United States and accounted for over 17 million physician office visits in the mid 1990's. Current estimates for the total cost of these diseases are in excess of $20 billion. These diseases are increasing in prevalence due to myriad causal factors, but principally driven by smoking.

While a chronic disease, the hallmark of asthma is acute episodes of difficulty breathing created by an acute constriction of smooth muscles lining the bronchi (the passage ways for air in the lungs), reducing the diameter of the airway and increasing the resistance to air flow. Bronchial constriction in asthma is "reversible" in that the acute constriction can be reversed by bronchodilation medication or by the passage of time (after removal of the irritant that elicited the constriction). However, asthma chronically exhibits itself as inflammation, hypertrophy, or hyper-excitability of the smooth muscles.

Emphysema and chronic bronchitis are different diseases than asthma, but can be related by the same causal factor and concomitant appearance in the same or similar individuals. Both emphysema and chronic bronchitis are predominantly caused by smoking and usually both exist in the same individual, hence they can be lumped together under the umbrella term Chronic Obstructive Pulmonary Disease (COPD). However, the diseases are very different and manifest themselves quite differently. While most subjects exhibit some amount of both diseases, a subject can be categorized by which condition is predominant in the subject's anatomy.

In emphysema, long term exposure to smoke or other noxious substances can result in a primary breakdown of the lung parenchyma (alveoli, etc.). Normal fine alveoli can break down and form large open "holes" (bullea), which in turn can result in reduced surface area for gas exchange, sapping of inhaled air flow from healthy lung tissue, or reduced anchoring of bronchi that can result in airway collapse.

In chronic bronchitis, irritation of the bronchi can result in inflammation, hypertrophy, or constriction of the smooth muscles lining the bronchi, or excessive mucus production that can clog the bronchi. While the smooth muscle contraction in chronic bronchitis is not as "reversible" as that exhibited in asthma, there is usually a significant degree of reversibility and bronchodilator medications can be used as a first line of therapy.

Overview

Chronic bronchitis and asthma can both exhibit airway smooth muscle constriction resulting in airway constriction. The present inventors have recognized, among other things, that bronchodilation medications can be used as a front lines therapy, but are far from optimal treatments, as the efficacy of bronchodilation medications can be limited and subject compliance is often poor between episodes of exacerbation. Further, the present inventors have recognized that inhalers are difficult to use properly and are especially difficult for the elderly (e.g., COPD) and children (e.g., asthma) to use optimally. Thus, the present inventors have recognized that a system or method configured to chronically dilate the bronchi such as by decreasing, inhibiting, or eliminating smooth muscle contraction would be beneficial for many subjects.

An implantable signal generator can be configured to generate a blocking signal to be delivered to at least a portion of a bronchus. The blocking signal can be configured to inhibit nerve traffic both to and from the lungs, to relieve bronchial smooth muscle contraction, and to inhibit cough. The implantable signal generator can be communicatively coupled to a processor configured to control delivery of the blocking signal, using received information about an indication of cough, to inhibit cough.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
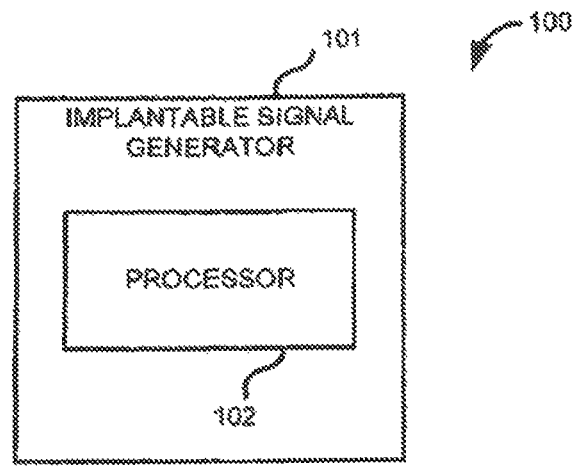
FIG. 1 illustrates generally an example of a system including an implantable signal generator and a processor.

The present inventors have recognized, among other things, a system and method for chronically dilating the bronchi, such as by decreasing, inhibiting, or eliminating smooth muscle contraction.

General Anatomy

In general, the peripheral nervous system can be divided into the somatic nervous system, the enteric nervous system, and the autonomic nervous system. The autonomic nervous system includes autonomic sensory neurons, integrating centers in the central nervous system (e.g., the brain), and autonomic motor neurons. A continual flow of nerve impulses from autonomic sensory neurons in visceral organs (e.g., afferent nerves) and blood vessels propagate into integrating centers in the central nervous system. Further, impulses in autonomic motor neurons (e.g., efferent nerves) can propagate to various effector tissues. This interaction between afferent and efferent propagation regulates the activity of smooth muscles and glands throughout the body.

Autonomic motor neurons have two principal branches: the sympathetic division and the parasympathetic division. Many organs have dual innervation from each of the branches. In general, nerve impulses from one division stimulates the organ to increase its activity (excitation), and impulses from the other division decrease the organ's activity (inhibition).

The balance between sympathetic and parasympathetic activity is termed "autonomic tone" and establishes the status of the organ. The balance is regulated by the hypothalamus, which typically turns up sympathetic tone while simultaneously turning down parasympathetic tone, and vice-versa.

High sympathetic tone supports body functions that support vigorous activity such as increased heart rate, increased blood pressure, etc. High parasympathetic tone supports "rest and digest" functions and has the opposite effect of sympathetic tone. Classically, human airway dilation was considered to be driven by the activation of the sympathetic division. However, other theories suggest that human airway smooth muscle is largely devoid of sympathetic innervation, and that dilation is derived from a different type of parasympathetic nerve.

Most parasympathetic nerves are termed "cholinergic" due to their use of the chemical acetylcholine during firing. Most sympathetic nerves are termed "adrenergic" due to their use of adrenal gland substances during firing. However, additional species such as non-cholinergic, non-adrenergic parasympathetic nerves exist.

The distribution and function of parasympathetic-cholinergic nerves is consistent across species. By contrast, the distribution and function of sympathetic and non-cholinergic parasympathetic innervation of airway smooth muscle varies considerably between species. Human airway smooth muscle is largely devoid of sympathetic adrenergic innervation. Non-adrenergic, non-cholinergic neurotransmitters (likely derived from the parasympathetic nerves) mediate the relaxations induced by the only demonstrably functional relaxant innervation of human airway smooth muscle.

In cats, guinea pigs, and ferrets, non-cholinergic parasympathetic transmitters are not co-released with acetylcholine from a single population of postganglionic parasympathetic nerves. Rather, an anatomically and functionally distinct parasympathetic pathway regulates non-adrenergic, non-cholinergic relaxations of airway smooth muscle. Reflexes differentially regulate the cholinergic and non-cholinergic nerves. Further, the parasympathetic innervation of human airways can be similar to that of cats and guinea pigs.

Both afferent and efferent parasympathetic nerves to the lungs derive from the vagus nerves at or near the pulmonary plexuses. The vagus nerves generally run roughly parallel to or lateral to the esophagus and trachea, while the plexuses are in turn further lateral than the vagi. The plexuses lie on or near the main bronchi near their bifurcation, and the nerves follow the branching of the bronchial tree within the lung parenchyma. Anantomists recognize both anterior and posterior plexuses (or equivalently the ventral and dorsal aspects). However, the anterior/ventral pulmonary plexus can be quite minor compared to the posterior/dorsal plexus. Further, the sympathetic innervation of the lungs pass through the pulmonary plexuses.

Basic Cholinergic Tone

Generally, airway parasympathetic nerves are tonically active during tidal breathing and typically produce a stable, readily reversible baseline obstruction of the airways reflecting opposing influences of contractile and relaxant airway parasympathetic nerves acting on airway smooth muscle.

Constriction of the smooth muscle by activation of efferent parasympathetic nerves can obliterate the lumen of small bronchi and bronchioles, markedly increasing airway resistance in larger, cartilaginous airways. Conversely, bronchodilation can be induced by withdrawing ongoing parasympathetic activity.

Sensory input from the lungs (e.g., via afferent nerves) can play a significant role in the creation of basal tone. Further, deregulation of basal tone, such as that seen in bronchitis or asthma, can originate from altered afferent signaling. A recurring presence and level of baseline tone in the airways can imply the existence of a "set point" for smooth muscle contraction. In certain examples, a withdrawal or augmentation of tone can be achieved in response to physiological or pathophysiological stimuli. Alterations in afferent or efferent nerve function can contribute to airway hyperresponsiveness and airway obstruction in diseases such as asthma or COPD.

In an example, cholinergic nerve activity in the airways can depend on input from afferent (e.g., mechanically sensitive) nerve fibers innervating the intrapulmonary airways and lungs. In certain examples, unilateral or bilateral severing of the afferent (sensory) nerves at the vagus can lead to a decrease in pulmonary resistance, indicating airway dilation.

In certain examples, such as during extreme circumstances (e.g., aspiration of foreign body, near drowning, trauma to the chest wall, etc.), a reflex bronchospasm may confer some physiologic benefit. Additionally, cholinergic tone may serve to minimize the work of breathing under the full variety of breathing states in a healthy individual (e.g., rest, exercise, etc). Further, afferent nerve signaling can be important for the maintenance of other functions, such as cough or mucus clearance. However, under non-extreme circumstances, the complete abolition of smooth muscle tone appears to have little or no physiological downside in a healthy individual. Moreover, in a diseased individual suffering from an obstructive disorder, the complete abolition of smooth muscle tone should be uniformly beneficial Vagotomy Generally, blocking the vagal nerves, such as by administering atropine sulfate to block postganglionic cholinergic pathways, by cooling of the nerve, or other blocking of the vagal nerves can result in dilation of the airways. Alternatively, surgical transaction of the vagus nerves can serve the same purpose. Historically, high vagal transection (in the neck region) has been used to treat asthma and COPD with some success. However, since the vagus nerve controls many body functions and organs other than the lungs, surgical transaction of the vagus carry significant complications and has not been adopted.

In a different example, lung transplant recipients can have denervated lungs while their vagus nerves are intact. In these subjects, bronchial diameters can be 150-200% of their normal pre-transplant bronchial diameter. While surgical pulmonary denervation can be an effective therapy for asthma or chronic bronchitis, the effect is typically short lived. The parasympathetic ganglia are typically located within the airways themselves. Generally, within the reimplanted lung, preganglionic fibers degenerate, but ganglia and undivided postganglionic fibers do not. In these instances, because the regenerating preganglionic axons are located only a few centimeters from the line of division, reinnervation can occur rapidly. In certain examples seen in animal models, pulmonary reinnervation can occur within a short period of time (e.g., three months), re-establishing autonomic tone.

Notably, other potentially beneficial side effects can be seen in subjects having denervated lungs. For example, mucus production can be decreased, and cough can be suppressed. In other examples, the sensation of dyspnea can be suppressed.

The present inventors have recognized, among other things, that a chronic, minimally invasive, and reversible system and method can be provided to increase the bronchial diameter of a subject. Further, the present inventors have recognized that while therapy can be directed toward the vagus nerves, there are benefits to directing the therapy more distally, toward the pulmonary parasympathetic nerves, thus limiting the effect to only the lungs and avoiding complications to other organs.

Mediastinoscopy

The mediastinum includes the region in mammals between the pleural sacs containing the heart and all of the thoracic viscera except the lungs. The mediastinum can be accessed using a minimally invasive procedure, such as mediastinoscopy or videomediastinoscopy. These minimally invasive procedures can generally be used to biopsy many of the lymph nodes in this region to aid in the staging determination of various cancers, and can generally be regarded as "day surgeries" having minimal morbidity and fast recovery.

In an example, mediastinoscopy can allow access to the trachea and to the main bronchi distal to the bifurcation. Access can be initiated at the suprasternal notch where dissection can be carried out down to the trachea. The plane of the pre-tracheal fascia can be used to carry the dissection down to the carina (bifurcation of the main bronchi). In another example, the Chamberlain procedure can allow access to the hilar areas of the lungs, e.g., using an initial incision at the 3rd intercostal space.

Mediastinoscopy can be performed by a thoracic surgeon with the subject under general anesthesia. While a host of large vascular structures run through this area, the procedure is generally safe and is the gold standard for lymph node biopsies, commonly having reported morbidity and mortality rates of 0.6% and 0.2%, respectively.

The pulmonary nerves located on the anterior and posterior aspects of the bronchi are available for therapy using the minimally invasive mediastinoscopic approach to the main bronchi.

Video-Assisted Thoracic Surgery

Mediastinoscopy typically does not expose the distal portion of the main bronchi or the dorsal aspect of the main bronchi. Thus, the present inventors have recognized that it may be advantageous to use other surgical techniques to access the bronchi.

In an example, video-assisted thoracic surgery (VATS) can be used to access structures on the thoracic wall (e.g., the sympathetic chain running parallel and lateral to the spinal column) or the lung itself (e.g., for a biopsy, wedge resection, etc.). In a VATS procedure, the lungs can be intubated with a bifurcated endotracheal tube, such that each lung can be ventilated independently. Thus, one lung can be ventilated while the other lung is deflated to provide working room in that side of the chest cavity.

In certain examples, one or more ports (typically less than 5) can be placed between ribs for access to the working space between the deflated lung and the intact chest wall. An elongate scope or camera can be inserted, as well as auxiliary tools, in one or more ports. While ports are typically used for convenience (to maintain easy access to insert and withdraw tools), a physical port is not strictly necessary. A port can include a physical port or a small incision between ribs without the physical port.

In an example, during a procedure, a subject can be positioned lying on one side with the upper arm raised overhead, thereby allowing the one or more ports to be placed in the ventral or dorsal portion of the chest wall and allowing the lung to be retracted either dorsally or ventrally. In an example, if a bilateral procedure is desired, the subject can be repositioned to the contralateral side during the procedure. In certain examples, the subject can be positioned in a prone posture so both sides of the chest cavity can be accessed without repositioning the subject. Further, the prone position allows the deflated lung to fall ventrally, naturally exposing the seam between the visceral and parietal pleura at the posterior (e.g., dorsal) aspect of the main bronchi. In other examples, other endoscopic procedures can be used to implant at least one of an electrode, a lead, or an implantable signal generator.

Therapy

In an example, surgical transection of the pulmonary nerves can abolish tonic smooth muscle tone. However, as discussed above, the duration of the effect can be limited. In certain examples, the duration can be as short as 3 to 12 months before re-innervation can occur.

As a result, several other approaches can be considered. In an example, the pulmonary nerves can be transected at several locations using a series of lesions (e.g., linear or other) created around at least a portion of the circumference of the bronchi. In an example, electrocautery can be used to create one or more linear lesions. In certain examples, two or more lesions can be created, separated by gaps, such as 2 mm to 15 mm gaps.

In other examples, an implant having a bioactive component or coating (e.g., that suppresses neuron growth or regeneration) can be attached or otherwise placed on or around the bronchi to prevent the severed nerves from reinnervating. In certain examples, the coating can be similar to or the same as the coating used on drug coated stents placed in the heart (e.g., paclitaxel or serolimus), which are known to suppress cellular proliferation In an example, an active implantable system, such as an implantable signal generator and lead system, can be provided, portions of which can be placed on or around the bronchi. Because afferent signals from the lungs are typically needed to produce the tonic smooth muscle tone, and because the tone is generally triggered by efferent parasympathetic fibers, substantially inhibiting or blocking nerve signals at the bronchi can serve the dual purpose of blocking both outgoing and incoming signals from the lungs. In this example, afferent signaling into the integrating centers in the central nervous system and outgoing signals to the smooth muscles can both be inhibited, effectively creating a "belt and suspenders" redundancy.

In an example, efferent and afferent parasympathetic and sympathetic nerve signals can be substantially inhibited or blocked at the bronchi. In certain examples, the inhibition or blocking can be accomplished without providing efferent or afferent stimulation (e.g., inducing action potentials) to the sympathetic or parasympathetic nerves at or near the bronchi.

Blocking

In an example, nerve "blocking" can be realized by placing one or more nerve cuffs or other electrodes near the post-ganglionic ascending afferent pulmonary nerves and post-ganglionic descending efferent pulmonary nerves on each pulmonary trunk. In other examples, the nerve "blocking" can be realized by placing one or more nerve cuffs on the pre-ganglionic vagus nerves on each pulmonary trunk, or by placing one or more other electrodes (e.g., nerve stimulation patch electrodes, such as an internal or external surface, plunge, or other electrode configuration) on the pulmonary nerve plexus or ganglia. In certain examples, other blocking electrodes can be placed elsewhere within or throughout the upper bronchial tree or trachea, e.g., to further or more finely control the blocking. In an example, one or more leads connecting one or more electrodes to a signal generator can exit the mediastinum through the surgeon's access route and can be tunneled subcutaneously from the suprasternal skin incision to a convenient location for the implanted signal generator.

In an example, the blocking signal can be on the order of 10-5000 Hertz (in some cases higher than 5000 Hertz), 0.1-10 mA, with a pulse width of 50 µs-2 ms. In other examples, other blocking signals having different ranges can be used, or a clamping signal, such as a voltage or current clamping signal, can be applied. In certain examples, the clamping signal can bias a cell such that an action potential can be prohibited.

Duty Cycle

In certain examples, the implantable system can be controlled using a duty cycle. In an example, because the signal generator is implantable, conservation of battery power can be important. Various duty cycling schemes can be applied to conserve power. In certain examples, the implantable system can include the ability to program electrostimulation duty cycle (e.g., on a percentage basis, such as from 1% to 100%; such as "on" for 5% of the stimulation period (1/frequency), on a recurring cycle duration basis, such as "on" for x of y seconds, such as "on" for 1 second out of 100 seconds up to "on" for 100 seconds out of 100 seconds, or other time measures, such as minutes, hours, or days).

Physiologic Adaption Avoidance and/or Functional Allowance

In an example, the implantable system can be programmed to pause therapy delivery for a variable amount of time and then have therapy resume, or to modify/modulate one aspect of therapy delivery, such as changing the stimulation frequency or duty cycle, in order to prevent the pulmonary system from adapting to the therapy stimulation sequence and to maintain therapy efficacy. In an example, the implantable system can be configured to provide a frequency hopping or varying frequency stimulation for anti-habituation.

In an example, the implantable system can activate, deactivate, increase, or decrease the blocking effect in response to one or more physiological or other parameter. In certain examples, the blocking can be increased or decreased in response to detected physical activity (e.g., physical activity sensed using a sensor, such as an accelerometer coupled to the implantable signal generator), the blocking can be activated or deactivated in response to sensed physiological parameters (e.g., a bronchial diameter decrease sensed using a sensor, such as a strain gauge, an impedance sensor, or other electrical, mechanical, or other sensor, etc.).

In an example, the implantable system can modulate the therapy based on a circadian or other rhythm of the subject (e.g., sensed using a sleep sensor, time of day, clock, or other sensor), or the implantable system can modulate the therapy to provide for one or more periods of no therapy (e.g., user selected time periods), or by abstaining from providing therapy to one side of the bronchi while the other side receives therapy or vice versa, for example, to allow the autonomic system to provide general pulmonary maintenance, such as coughing, mucus clearance, mucus production, or other physiological response. For example, COPD subjects can be particularly susceptible during the early morning hours to exacerbation. As such, maximum therapy can be desirable during this time period.

In other examples, the implantable system can be configured to deliver therapy during time periods of peak constriction or discomfort. Many subjects have identifiable periods of maximum constriction or discomfort, such as in the morning following sleep, in the evening before sleep, or during one or more other time periods. In an example, the implantable sensor can include a sleep sensor or posture sensor configured to detect and to inhibit therapy during sleep, or configured to provide therapy following the detected cessation of sleep. In an example, periods of maximum therapy or no therapy can be configured using population data, or can be configured using specific subject data. In an example, the implantable system can initially be configured using population or clinical data, and then can be adjusted according to individual subject needs.

For example, if a specific subject commonly reports waking at or near a specified time during sleep feeling short of breath or having discomfort, the implantable system can be configured to provide therapy around the reported time, relieving the discomfort of the subject. Further, therapy can automatically be provided following a detected cessation of sleep. If the detected cessation is during a normal sleep time of the subject, indicating that airway restriction or subject discomfort caused the subject to wake, therapy can be provided.

In an example, the implantable system can be configured to cease therapy during periods where therapy is not needed. In an example, the periods can be identified using information from the subject, from a population, or the periods can be user-specified. For example, certain subjects feel little to no constriction or discomfort during the afternoon. In this example, to conserve battery life, or to allow normal physiological response of the subject to resume, therapy can be prohibited during the identified period.

In other examples, therapy can be switched off during periods of exacerbation, such as COPD exacerbation. In an example, COPD exacerbation can include a worsening of COPD symptoms beyond normal day-to-day variation. In an example, exacerbation can be sensed using one or more physiological parameters configured to monitor symptoms of COPD, such as breathlessness, cough, sputum or mucus production, color, or thickness, wheezing, thoracic pressure (e.g., chest tightness, pressure, or pain, etc.), or one or more other symptoms. In other examples, the implantable system can receive one or more other indicators of exacerbation, such as hospitalization, or one or more other user inputs indicating exacerbation.

In an example, therapy can be switched off during hospitalization, or during one or more other physiological or time periods specified by a clinician. Hospitalization can be manually input, or automatically determined using medical record data or one or more other source of medical information.

Cough

In an example, inhibiting nerve traffic to one or more lung, from one or more lung, or both to and from one or more lung along one or more of the bronchi can block, inhibit, or reduce the urge of a subject to cough, for example, by reducing the ability of one or more of the bronchi to contract, or by blocking afferent signals from receptors responsive to gas, toxins, foreign matter, etc.

In an example, the implantable system can include one or more sensor (e.g., cough sensor) or input configured to receive an indication of acute or chronic cough, such as a pressure sensor, a respiration sensor, a sound sensor, an activity sensor, an impedance sensor, a phrenic nerve input, or other sensor configured to detect or receive an indication of cough. In an example, the pressure sensor can be configured to detect a change in pressure in a body (e.g., airway, thorax, etc.) indicative of a cough. In an example, the respiration sensor (e.g., tidal volume sensor, minute ventilation (MV) sensor, etc.) can be configured to detect a change in respiration indicative of a cough. In an example, the sound sensor (accelerometer, microphone, etc.) can be configured to detect a change in sound indicative of a cough. In an example, the activity sensor (e.g., accelerometer, etc.) can be configured to detect a vibration, motion, or other activity of a subject indicative of a cough. In an example, the impedance sensor can be configured to detect impedance (e.g., a change in impedance) indicative of fluid (e.g., mucus, etc.) buildup, accumulation, or a change in consistency of the lungs, bronchi, or airway indicative of a likely period of cough, or mucas buildup. In an example, one or more electrodes can be used to sense or detect phrenic nerve (or other nerve) activity indicative of cough.

In an example, upon sensing or detecting acute or chronic cough, the implantable system can be configured to inhibit nerve traffic along one or more of the bronchi, blocking, inhibiting, or reducing the ability of a subject to cough. In other examples, the implantable system can be configured to deliver therapy upon sensing or detecting a series of coughs, or coughing or a rate of coughing over a specified (e.g., user specified) period of time (e.g., 1 minute, 5 minutes, etc,). In an example, the inhibition can continue for a period of time (e.g., a time period established by a clinician), after which, the therapy can cease, only to resume if the coughing continues or begins again following therapy.

In other examples, the implantable system can include one or more user-inputs configured to receive a user indication of cough, or a user-indicated cough event (e.g., a subject, clinician, or other caregiver indication of cough, a subject-indicated, clinician-indicated, or other caregiver-indicated cough event, etc.). In an example, the implantable system can be configured to receive input from an external device configured to receive input from the user. In an example, the external device can include a subject control. As the subject experiences a cough or series of coughs, the subject can provide a request, using the external device, to the implantable system to provide blocking therapy. In other examples, the external device can include a medical device programmer, or other clinician operated device. As the subject is being treated for cough (e.g., chronic cough), the clinician or other caregiver or user can provide a request to the implantable system, using the external device, to provide blocking therapy to treat the coughing. Upon receiving the request or indication of cough, the implantable system can deliver the blocking therapy, inhibiting nerve traffic both to and from the lungs, treating the cough.

In an example, after sensing or detecting cough, or upon receiving a user indication of cough, the blocking therapy can be delivered. In an example, the blocking can be delivered for a period of time and then stopped to ascertain whether the coughing or cough episode has ceased. In other examples, the blocking can be delivered until the sensing or detecting an indication of cough has detected a cessation of cough, or the blocking can be delivered until a user identified cessation of cough is received. If coughing continues, then the blocking signal can be resumed.

In other examples, the implantable system can be configured to allow cough (e.g., by stopping therapy), such as for mucus, sputum, or other matter clearance during one or more therapy programs. Further, by blocking or inhibiting neural traffic on at least a portion of the bronchi, mucus production can be inhibited or reduced by blocking efferent signals configured to trigger mucus production.

Pulmonary Toilet

In an example, certain subjects (e.g., having chronic bronchitis, etc.) can benefit from productive cough, by allowing mucus or other foreign matter to escape the lungs or bronchi. In an example, the mucus or other foreign matter can be detected, such as by using a mucus or other sensor. In other examples, a user (e.g., a subject, a clinician, or other caregiver or user) can be configured to provide a normal or other period of time where no therapy is to be delivered (e.g., no blocking signal is to be provided to the subject), to allow for clearance of mucus or other matter.

In an example, the time period can include a daily, hourly, or other normal or other period configured to allow a time for normal pulmonary maintenance, or to allow for the clearance of mucus or other matter in the absence of, or in conjunction with, detected mucus or other foreign matter buildup.

In an example, the time period can include a preset daily period (e.g., 15 minutes, 1 hour, etc.) occurring at a specific time of day (e.g., 8 AM, 10 PM, etc.). In other examples, the time period can include a period of time after the subject has woken from sleep. In certain examples, a sleep sensor, subject activity or posture sensor, or other sensor can be used to detect a sleep or awake state of the subject.

In other examples, the time period can include a more regular interval, such as "off" for 15 minutes and "on" for 45 minutes, "off" for 5 minutes and "on" for 1 hour, etc.

Hyperinflation

In an example, the implantable system can be configured to detect and apply therapy during periods of hyperinflation. Hyperinflation occurs as inhalation increases faster than exhalation. In a healthy subject, as inhalation increases (e.g., during activity), exhalation increases to expel the increased volume of air. However, if inhalation increases and exhalation does not increase, the subject's respiration baseline approaches the maximum respiration capacity of the lungs, leaving the subject short of breath and starved of oxygen. By dilating the bronchi, more air can be allowed to escape, increasing the ability of the subject to exhale.

In an example, hyperinflation can be detected by a combination of factors, such as an increase in subject activity (e.g., indicative of an increased respiratory need), an increase in breathing frequency, or a decrease in respiration volume. Once hyperinflation is detected, therapy can be provided or increased to increase the diameter of the bronchi, opening the airway.

Titrate Therapy with Drug Stimulation

In an example, the implantable system can be configured to provide the blocking signal in conjunction with drug stimulation. Many COPD subjects take a drugs (e.g., spiriva, etc.) configured to prevent bronchospasm (narrowing of the airway), or to provide airway dilation. In an example, the implantable system can be configured to work with the drug stimulation to increase total efficacy of therapy.

For example, many subjects taking anticholinergic agents, such as spiriva, do so at set times (e.g., daily in the morning, etc.). Using the dosage and instructions for use, blocking therapy can be provided as the effects of the anticholinergic begin to decrease, thereby extending the total effect of therapy.

In an example, if a subject receives a dose of an anticholinergic agent in the morning, the effect (e.g., measured forced expiratory volume (FEV)) increases initially, peaks, then gradually falls off. In an example, as the effect of the drug begins to decline, blocking therapy can be provided to extend the total effect of therapy (e.g., by increasing the total expiratory volume). In an example, once the subject is determined to be asleep, or once the subject is instructed to receive another dose of the anticholinergic agent, blocking therapy can be ceased.

Hyperplasia and Hypertrophy

Many COPD subjects have an enlarged, thick, or bulked bronchi reducing the diameter of the airway due to hyperplasia (cell multiplication), hypertrophy (cell enlargement, muscle bulk), or both. In order to achieve maximum dilation of the bronchi, the muscles of the bronchi must be at rest, or debulked. In an example, providing a blocking signal and relieving smooth muscle contraction can relax the muscles of the bronchi, over time, leading to a debulking of tissue or a loss of smooth muscle tone.

In an example, a narrow bronchial passage can be detected using a detected pressure through the airway, using a detected volume of air through the airway, or using a relationship between both. In certain examples, pressure can be detected in the bronchi. In other examples, other surrogates can be used, such as airway pressure in other parts of the respiratory system. In an example, an airway pressure or volume can be detected using temperature sensors, detecting an air temperature drop along a pathway.

In an example, once a narrow bronchial passage has been detected, therapy can be provided to relieve smooth muscle contraction. In certain examples, the blocking therapy can be combined with one or more other debulking techniques, such as ablation, etc.

Pulse Generator

In an example, an implantable signal generator can be configured to receive information from at least one sensor or other system component and modulate the blocking signal using the received information. In an example, the system component can include a component, such as a processor or other sensor or module, capable of generating an internally generated event, such as a clock or other marker or trigger.

In other examples, the sensor can include one or more other physiologic or other sensors configured to sense physiologic or other information from the subject.

Programmer

In an example, the system can include a clinician programmer configured to be communicatively coupled (e.g., wirelessly coupled) to at least a portion of the implantable system, such as the implantable signal generator, etc. In an example, the clinician programmer can be configured to receive information from, or send information to, the implantable signal generator. In other examples, the clinician programmer can allow a clinician or other user to program or otherwise send instructions to the implantable signal generator.

Subject Actuator

In an example, the system can include a subject programmer or subject actuator configured to be communicatively coupled to at least a portion of the implantable system. In an example, the subject programmer can provide for communication between the clinician programmer and the implantable system, such as by acting as a repeater. The subject programmer can be configured to communicate locally with the implantable system, and remotely with the clinician programmer.

In an example, the subject programmer can be configured to allow a subject to control, alter, or otherwise change at least one operating characteristic of the implantable system. In an example, the subject can turn the implantable system on or off using the subject programmer or subject actuator. In other examples, the subject programmer can be configured to communicate information to or from the subject to a clinician or the implantable system.

Battery

In other examples, the implantable system can include one or more other aspects, such as a primary or secondary cell battery system having various charging or re-charging capabilities. The battery system can include a primary cell, a secondary cell (e.g., rechargeable), or other topology. The secondary cell topology can include or be coupled to a charging system, such as an inductively coupled, acoustically coupled, photonically coupled, or other coupled charging system.

Battery Charger

In an example, the system can include a battery charger. The battery charger can include implantable components included in or coupled to the implantable system, external components, or a combination of implantable and external components. In an example, the battery charger can be configured to wirelessly charge (e.g., inductively, etc.) the implantable system. In an example, the implantable signal generator can be implanted subcutaneously outside of the thorax, e.g., accessible for maintenance, battery charging or replacement, or for communication outside of the body.

Lead/Electrode

In an example, implantable system can include a multi-lead or multi-lead multi-channel system. The multi-lead system can include one or more leads, each having one or more electrodes. In certain examples, the leads or the electrodes can be electrically coupled, or can be electrically independent from each other. In other examples, the leads or electrodes can be electrically (e.g., directly, such as through a lead) coupled to an implantable signal generator, or the leads or electrodes can be wirelessly coupled to the implantable signal generator, such as by using one or more wireless transceivers or communication modules.

For example, a wireless lead can be implanted at the pulmonary nerves and communicate wirelessly with an implantable signal generator. Alternatively, a wireless lead could be placed endo-bronchially (without surgery) and communicate with an implantable signal generator.

Telemetry

Further, the implantable system can include a telemetry system, configured to communicate between the implantable system and an external device, such as unidirectionally or bidirectionally. The implantable system can be configured communicated wirelessly with the external device, such as by inductive, RF, or other telemetry. The communication can be configured to transfer information between the implantable system and the external device, such as one or more of programming information, physiological information, or other instructions or information.

Example Procedural Description and Steps

Intubate subject with a bifurcated endotracheal tube.

Position subject in lateral recumbent position with arm raised over head, exposing both anterior and posterior chest walls on operative side.

Ventilate subject on non-operative side only.

Make skin incisions and place ports using blunt dissection at desired locations on the anterior and posterior chest wall, typically from the $4^{th}$ through $8^{th}$ rib interspaces.

Lung will collapse spontaneously once chest wall is violated and ET tube is allowed to vent on operative side.

Insert thorascope and auxiliary tools through ports.

A combination of subject positioning (slightly rolled forward) and retraction may be used to cause the lung to roll anteriorly, exposing the reflection of the parietal and visceral pleura.

Use careful blunt and sharp dissection to incise the reflection of the pleura at the bronchus.

Bluntly dissect connective tissue to isolate the bronchus at a distance approximately 1 to 4 cartilaginous "rings" from where the bronchus enters the lung parenchyma.

Care must be taken to avoid damage to the aorta or azygous vein (depending on side of surgery), pulmonary artery, and pulmonary vein.

Attach cuff electrode (with attached lead) to the dorsal aspect of the bronchus at a distance approximately 1 to 4 "rings" from the lung parenchyma.

Note: alternative electrode configurations may require different attachment techniques. In the case of a loop electrode, blunt dissection is carried out around the complete circumference of the bronchus. A suture may be passes around the bronchus, which can then be used in turn to pull an electrode around the bronchus.

Loop the lead superiorly over the hilum of the lung, being careful not to kink, twist, or apply tension to the lead.

The lead may also be tunneled under the pleura for a distance along the inside of the chest wall.

At the desired location, typically on the anterior chest wall, the lead may be tunneled between the ribs. On the exterior chest, the led may be tunneled subcutaneously to a desired location for the signal generator, typically near the clavicle or on the abdominal wall.

Re-inflate the collapsed lung and reposition the subject to the contralateral side.

Place the second electrode and lead analogously to the first.

Test each lead for appropriate and correct electrical contact and functioning.

Create a subcutaneous pocket for the signal generator at the desired location.

Attach both leads and turn on the signal generator.

Insert bilateral chest tubes and close all incisions.

Chest tubes may be removed approximately 24 hours post operatively once a chest X-ray confirms the absence of clinically significant pneumothorax and/or pleura effusion.

In an example, a subject can be intubated, such as by using a bifurcated endotracheal tube or other appropriate medical instrument.

In an example, the subject can be positioned in a lateral recumbent position with arm raised overhead, exposing both anterior and posterior chest walls on operative side. In other examples, the subject can be positioned in one or more other positions allowing access to the lungs.

In an example, the subject can be operated on a first side only, and can be ventilated on the non-operative side. In an example, skin can be made and ports can be placed using blunt dissection at one or more desired locations on the anterior or posterior chest wall. In an example, the desired locations can be located between the 4th through 8th rib interspaces.

Once the chest wall is violated, the lung can collapse, and the endotracheal tube can be used to provide ventilation on the operative side. Once the lung is collapsed, medical instruments, such as a thorascope or auxiliary tools, can be inserted through the ports.

In certain examples, a combination of subject positioning (slightly rolled forward) and retraction can be used to cause the lung to roll anteriorly, exposing the reflection of the parietal and visceral pleura.

Once exposed, a careful blunt and sharp dissection can be used to incise the reflection of the pleura at the bronchus. From there, connective tissue can be bluntly dissected to isolate the bronchus, e.g., at a distance approximately 1 to 4 cartilaginous "rings" from where the bronchus enters the lung parenchyma. Care must be taken to avoid damage to the aorta or azygous vein (depending on side of surgery), pulmonary artery, and pulmonary vein.

In an example, an electrode, such as a cuff electrode (with attached lead) can be attached to the dorsal aspect of the bronchus at a distance approximately 1 to 4 "rings" from the lung parenchyma. In certain examples, alternative electrode configurations can require different attachment techniques. For example, in the case of a loop electrode, blunt dissection can be carried out around the complete circumference of the bronchus. A suture can be passed around the bronchus, which can then be used in turn to pull an electrode around the bronchus.

In an example, a lead coupled to the electrode can be looped superiorly over the hilum of the lung, being careful not to kink, twist, or apply tension to the lead.

In certain examples, the lead can also be tunneled under the pleura for a distance along the inside of the chest wall. At the desired location, typically on the anterior chest wall, the lead can be tunneled between the ribs. On the exterior chest, the led may be tunneled subcutaneously to a desired location for the signal generator, typically near the clavicle or on the abdominal wall.

In an example, the collapsed lung can be re-inflated, and the subject can be repositioned to the contralateral side. Once re-positioned, the subject can be operated on the second side, previously non-operative side. Similar steps can be followed to place a second electrode on the second side analogously to the first electrode. Once implanted, each lead for each electrode can be tested for appropriate and correct electrical contact and functioning.

In an example, a subcutaneous pocket can be created for the signal generator at a desired location. Once the pocket is created, and the signal generator is placed, both leads can be attached and the signal generator can be turned on.

In an example, bilateral chest tubes can be inserted and all incisions can be closed. Following a recovery period, (e.g., 24 hours), and successful testing to confirm the absence of clinically significant pneumothorax or pleura effusion (e.g., using a chest X-ray or other method), the chest tubes can be removed.

In other examples, one or more other methods can be used to implant the signal generator and provide one or more electrodes coupled to or proximate one or more of the bronchi.

FIG. 1 illustrates generally an example of a system 100 including an implantable signal generator 101 and a processor 102 coupled to the signal generator 101. In certain examples, the processor 102 can be included in, or can be separate from the implantable signal generator 101. In an example, the processor 102 can include an external component configured to be wirelessly coupled to the implantable signal generator 101.

In an example, the implantable signal generator 101 can be configured to generate a blocking signal to be delivered to at least a portion of a bronchus of a subject. In an example, the blocking signal can be configured to inhibit efferent nerve traffic, afferent nerve traffic, or both efferent and afferent nerve traffic between the central nervous system and at least a portion of the bronchus or a lung. In an example, the blocking signal can be configured to relieve bronchial smooth muscle contraction, and can inhibit cough, e.g., by blocking nerve signals to and from the respiratory anatomy.

In an example, the processor 102 can be configured to receive information about an indication of cough. In certain examples, the information can include information from a user-identified indication of cough, the information can include information from a sensor configured to detect an indication of cough, or the information can include information from both the user-identified indication and the sensor. In an example, the processor 102 can be configured to control delivery of the blocking signal to the at least a portion of the bronchus, e.g., to inhibit cough.

Figure 2:
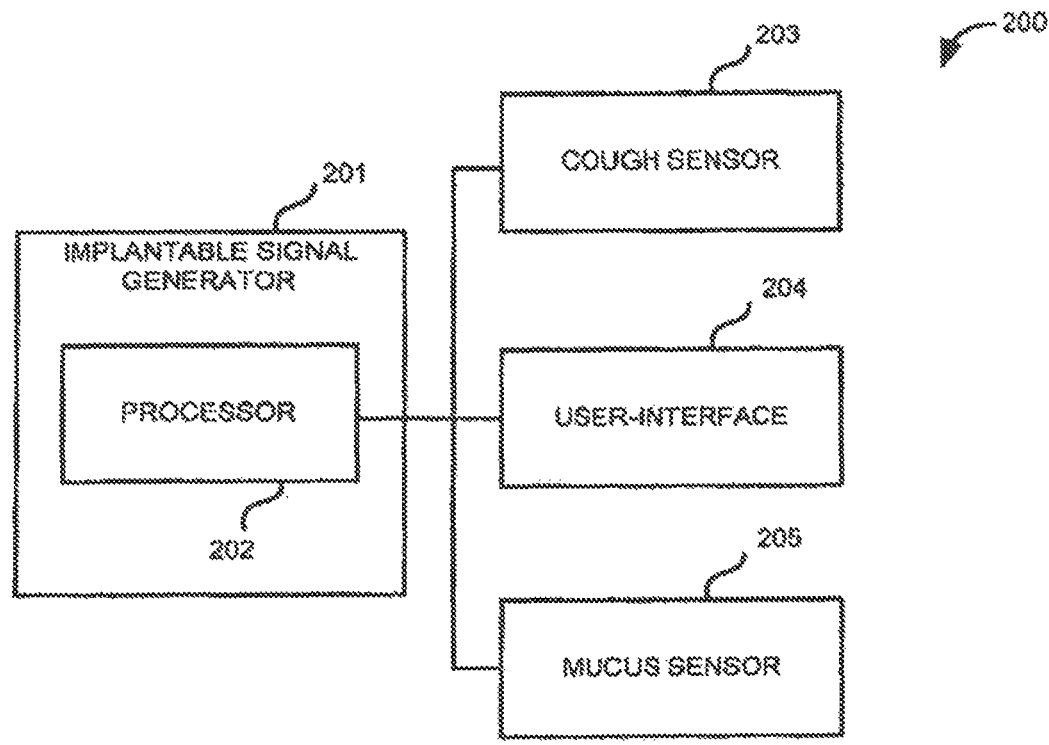
FIG. 2 illustrates generally an example of a system including a cough sensor, a user-interface, and a mucus sensor.

FIG. 2 illustrates generally an example of a system 200 including an implantable signal generator 201 and a processor 202 coupled to the signal generator 201. In certain examples, the system 200 can include at least one of a cough sensor 203, a user-interface 204, or a mucus sensor 205 coupled to the processor 202.

In an example, the cough sensor 203 can include one or more implantable or external sensors configured to detect an indication of cough. In an example, the cough sensor 203 can be configured to detect a cough or an episode of one or more coughs, and to provide information about the detected cough or episode or one or more coughs to at least one of the processor 202 or the signal generator 201.

In an example, the user-interface 204 can include one or more user-inputs configured to receive information from a user (e.g., a subject, a clinician, a caregiver, or other user). In an example, the user-interface 204 can be configured to receive information about an indication of cough from the user, and to provide information about the indication of cough to at least one of the processor 202 or the signal generator 201.

In an example, the user-interface 204 can include a subject-interface, configured to allow the subject to identify an undesired period of cough, e.g., by pushing a button or providing one or more other inputs. In an example, information about the subject-identified undesired period of cough can be provided to at least one of the processor 202 or the signal generator 201.

In an example, the mucus sensor 205 can include one or more implantable or external sensors configured to detect mucus or other matter, or to detect a building or accumulation of mucus or other matter in the lungs or bronchi. In an example, the mucus sensor 205 can include an impedance sensor, or other sensor configured to detect the buildup or accumulation of mucus or fluid in the lungs or bronchi. In an example, the mucus sensor 205 can be configured to provide information about the detected mucus or other matter to at least one of the processor 202 or the signal generator 201.

Figure 3:
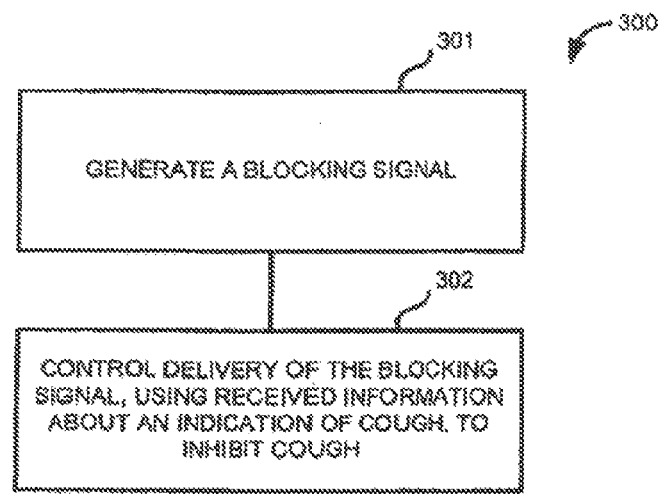
FIG. 3 illustrates generally an example of a method including controlling delivery of a blocking signal to inhibit cough.

FIG. 3 illustrates generally an example of a method 300 including controlling delivery of a blocking signal to inhibit cough.

At 301, a blocking signal can be generated. In an example, the blocking signal is generated using a signal generator, such as the implantable signal generator 101.

At 302, information about an indication of cough is received, and delivery of the blocking signal is controlled, using the received information, to inhibit cough.

Figure 4:
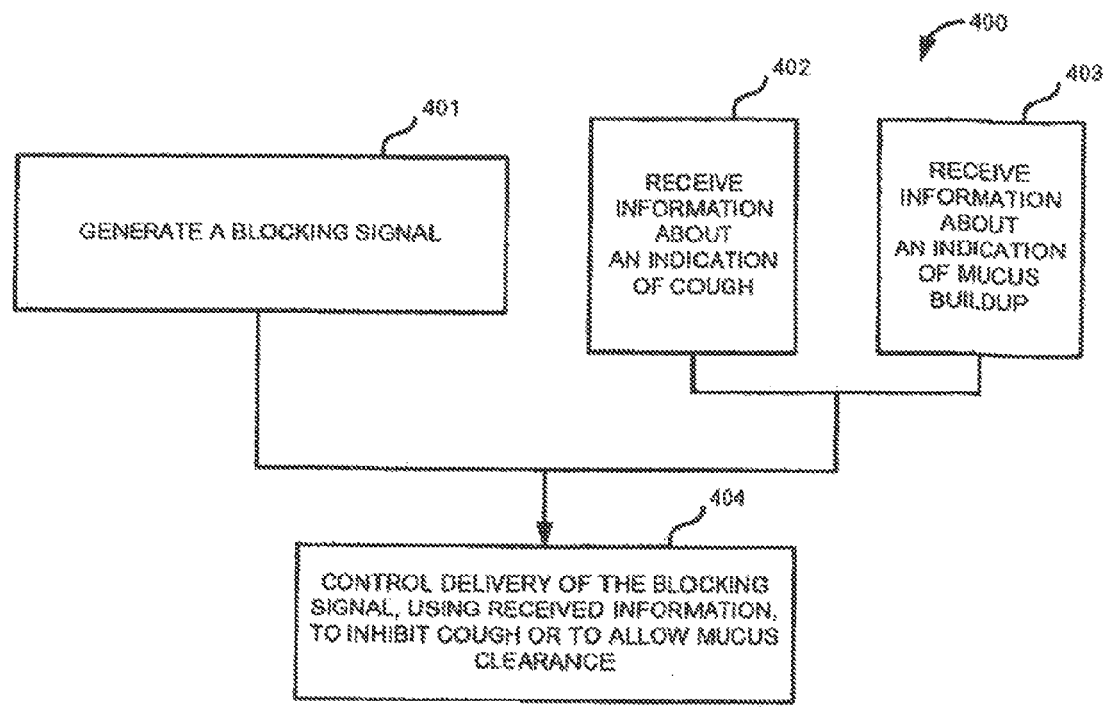
FIG. 4 illustrates generally an example of a method including controlling delivery of a blocking signal to inhibit cough, or to allow mucus clearance.

FIG. 4 illustrates generally an example of a method 400 including controlling delivery of a blocking signal to inhibit cough, or to allow mucus clearance.

At 401, a blocking signal is generated, for example, using a signal generator, such as the implantable signal generator 101.

At 402, information about an indication of cough is received. In an example, the indication of cough can be received from at least one of a cough sensor (e.g., the cough sensor 203 or other sensor configured to detect an indication of cough) or a user-interface (e.g., the user-interface 204 or other user-input configured to receive a user-identified cough indication).

At 403, information about an indication of mucus building is received. In an example, the indication of mucus building can be received from a mucus sensor, such as the mucus sensor 205 or other sensor configured to detect an indication of mucus or fluid accumulation in at least one of a lung or bronchi.

At 404, delivery of the blocking signal can be controlled, using received information, to inhibit cough or to allow mucus clearance. In an example, the delivery of the blocking signal can be controlled using the received information about the indication of cough, about the received information about the indication of mucus buildup, or both. In an example, the controlling the delivery of the blocking signal can include providing the blocking signal to at least a portion of the bronchi if an indication of cough is detected or received. In other examples, the controlling the delivery of the blocking signal can include not providing the blocking signal if an indication of mucus buildup or other fluid or foreign matter is detected or received.

Figure 5:
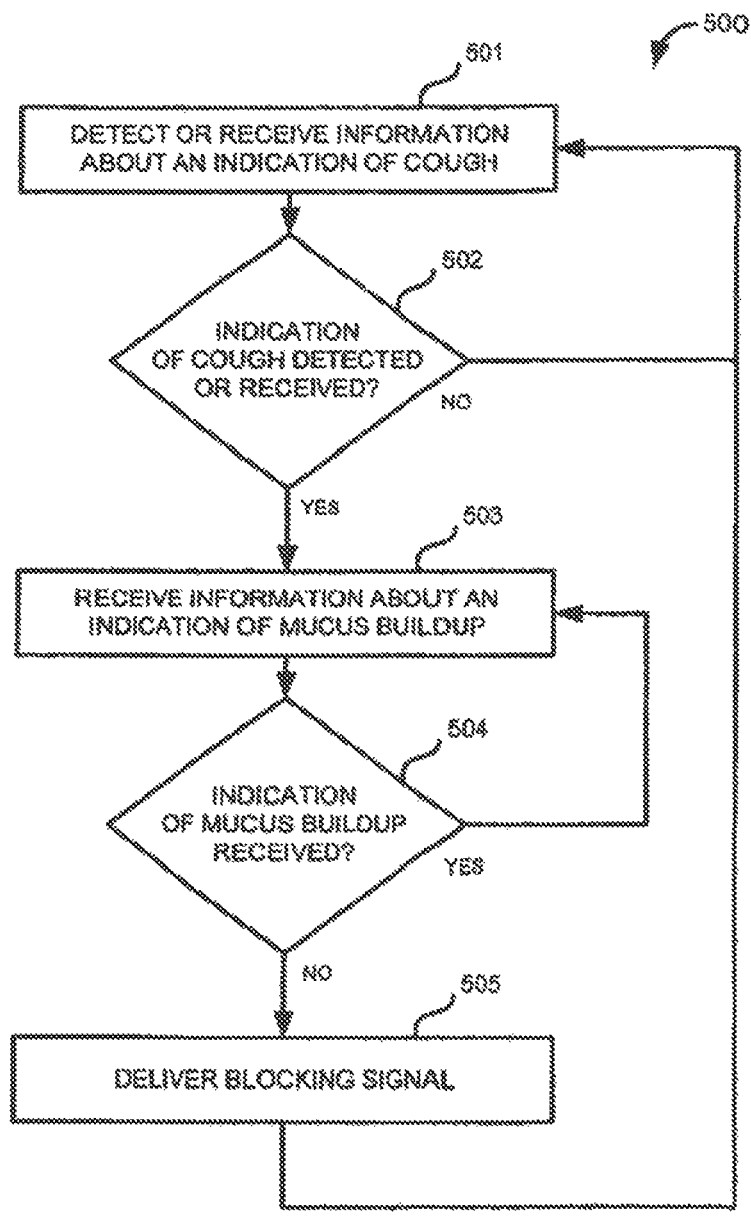
FIG. 5 illustrates generally an example of a method including delivering a blocking signal.

FIG. 5 illustrates generally an example of a method 500 including delivering a blocking signal.

At 501, information about an indication of cough is detected or received. In an example, the information can be detected or received using at least one of a cough sensor (e.g., the cough sensor 203 or other sensor configured to detect an indication of cough) or a user-interface (e.g., the user-interface 204 or other user-input configured to receive a user-identified indication of cough).

At 502, if an indication of cough is detected or received, then, at 503, information about an indication of mucus buildup is received. At 502, if an indication of cough is not detected or received, then process flow returns to 501.

At 504, if the information about the indication of mucus building indicates that mucus has not built up, then, at 505, a blocking signal is delivered configured to inhibit cough. In an example, a blocking signal can be delivered to at least a portion of a bronchus using an implantable signal generator. In an example, the blocking signal can be configured to inhibit nerve traffic both to and from the lungs, relieving bronchial smooth muscle contraction and inhibiting cough. In other examples, the blocking signal can be configured to inhibit mucus production.

At 504, if the information about the indication of mucus building indicates that mucus has built up, then process flow returns to 503. In an example, once the mucus buildup is cleared, e.g., by cough, then the blocking signal can be delivered to inhibit cough. In certain examples, the blocking signal can be ceased for a specified time to allow for mucus clearance, or the blocking signal can be ceased until an indication of mucus or fluid clearance is received using the mucus sensor.

In certain examples, if cough continues, but mucus is not cleared, information can be provided to a user, a clinician, or other caregiver, such as using an alarm or other notification. In other examples, other information, such as the information about the indication of cough or mucus buildup, can be provided.

Figure 6A:
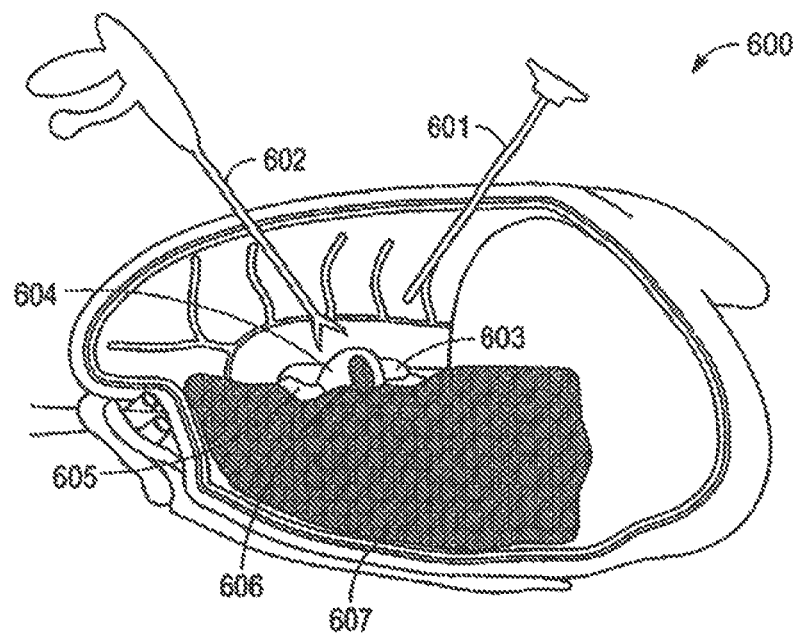
FIGS. 6A-6B illustrate generally structures in a thorax during access.
Figure 6B:
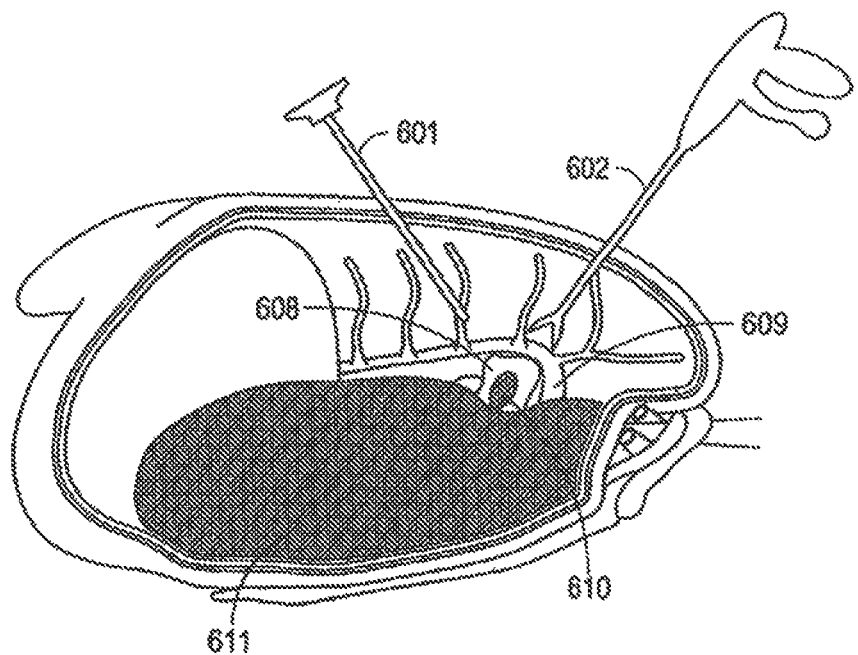

FIGS. 6A and 6B illustrate generally structures in a thorax during access, including an incised pleura at a parietal-visceral reflection. FIG. 6A illustrates a left mediastinum exposure, including a left inferior pulmonary vein 603, a left main bronchus 604, a left pulmonary artery 605, a left posterior pulmonary plexus 606, and a deflated left lung 607. FIG. 6B illustrates a right mediastinum exposure, including a right main bronchus 608, an azygous vein 609, a right posterior pulmonary plexus 610, and a right lung 611.

In these examples, a first instrument 601, such as a fiberscope, a thoracoscope, or other instrument, can enter the thorax, such as into the sixth rib interspace, and a second tool 602, such as a dissection tool or other instrument, can enter the thorax, such as into the fourth rib interspace. In other examples, at least one of the first or second instruments 601, 602, can access the thorax at one or more other locations.

Generally, working between the spine and its associated vascular structure and the deflated lung, an incision in the pleura can be made at the reflection of the parietal pleura and the visceral pleura allowing access to the dorsal aspect of the main bronchi. In the example of FIG. 6A, a descending aorta is close to the spinal column and is left undisturbed. In the example of FIG. 6B, the azygous vein 609 is close to the spinal column and is left undisturbed. In an example, once the dorsal aspect of the main bronchi has been accessed, an electrode (e.g., a cuff electrode, patch electrode, etc.) can be affixed to the dorsal aspect of the main bronchi near where the bronchi enter the lung parenchyma.

FIGS. 7-10 illustrate generally examples of various signal generator implant sites, lead paths, electrode sites, and electrode configurations.

Figure 7:
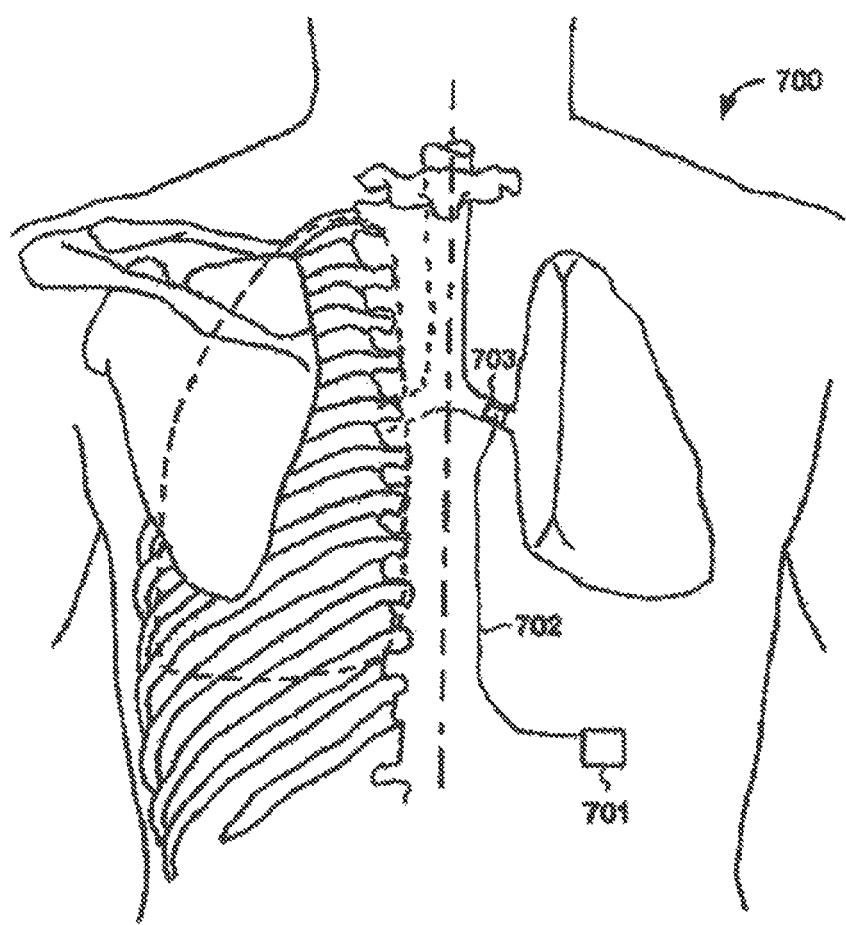
FIGS. 7-10 illustrate generally examples of various signal generator implant sites, lead paths, electrode sites, and electrode configurations.

FIG. 7 illustrates generally an example of a system 700 including an implantable signal generator 701, a lead 702 coupled to the implantable signal generator 701, and an electrode 703 coupled to the lead 702. In this example, the electrode can be affixed to or otherwise associated with the dorsal aspect of the main bronchi. The lead can be attached to the electrode and can exit the thoracic cavity between the ribs. While other exit locations can be used, it can be convenient to use the existing access port. Once the lead exits the thoracic cavity, it can be tunneled subcutantiously to a convenient location for placing the implantable signal generator.

In the example of FIG. 7, the implantable signal generator is located in a low lumbar, pararenal location. In other examples, the implantable signal generator can be located in other locations in the body, such as in the thorax, or other subcutaneous locations. In other examples, the signal generator can be located outside of the body, with the lead exiting to connect externally.

Figure 8:
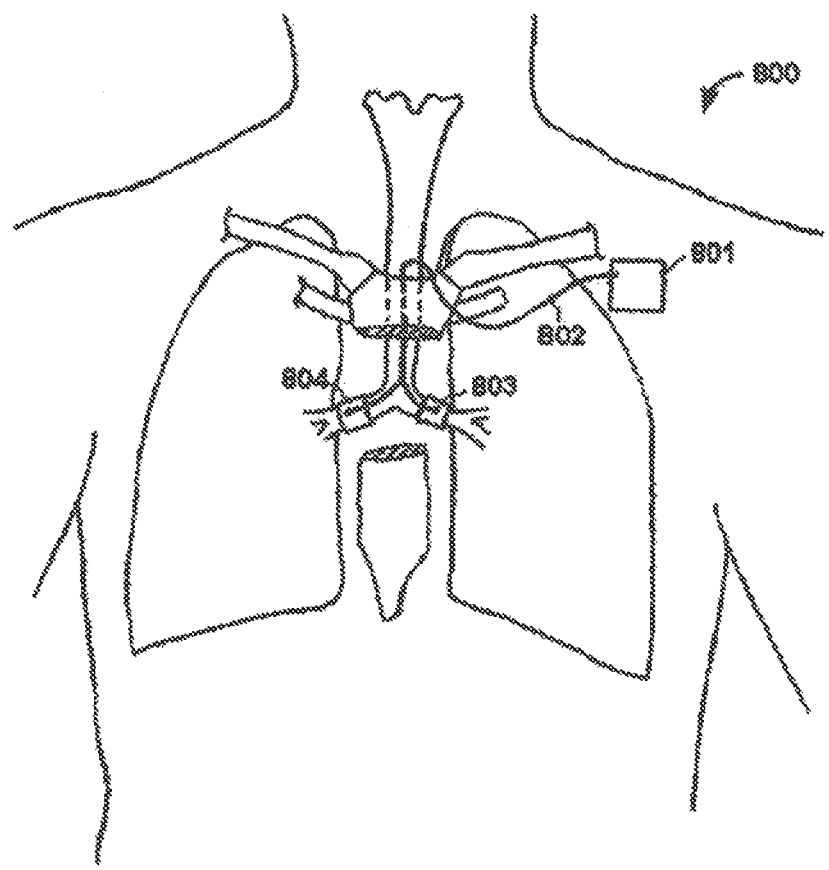

FIG. 8 illustrates generally an example of a system 800 including an implantable signal generator 801, a lead 802 coupled to the implantable signal generator 801, and first and second cuff electrodes 803, 804 coupled to the left and right bronchi.

Figure 9:
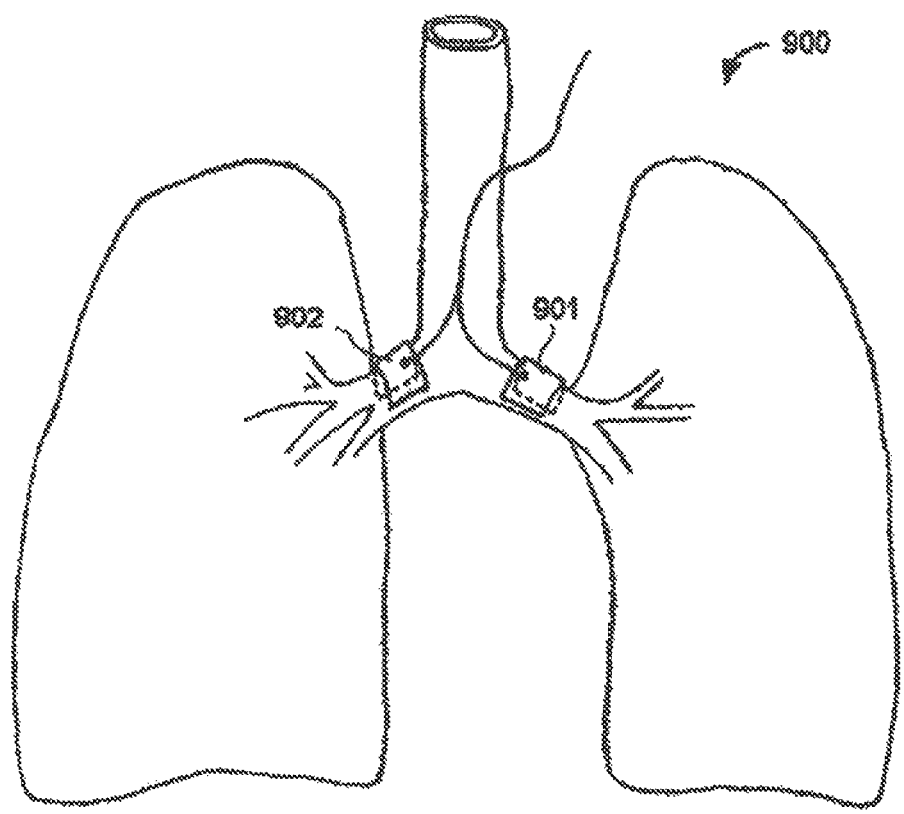

FIG. 9 illustrates generally an example of a system 900 including first and second partial cuff electrodes 901, 902 coupled to the left and right bronchi.

Figure 10:
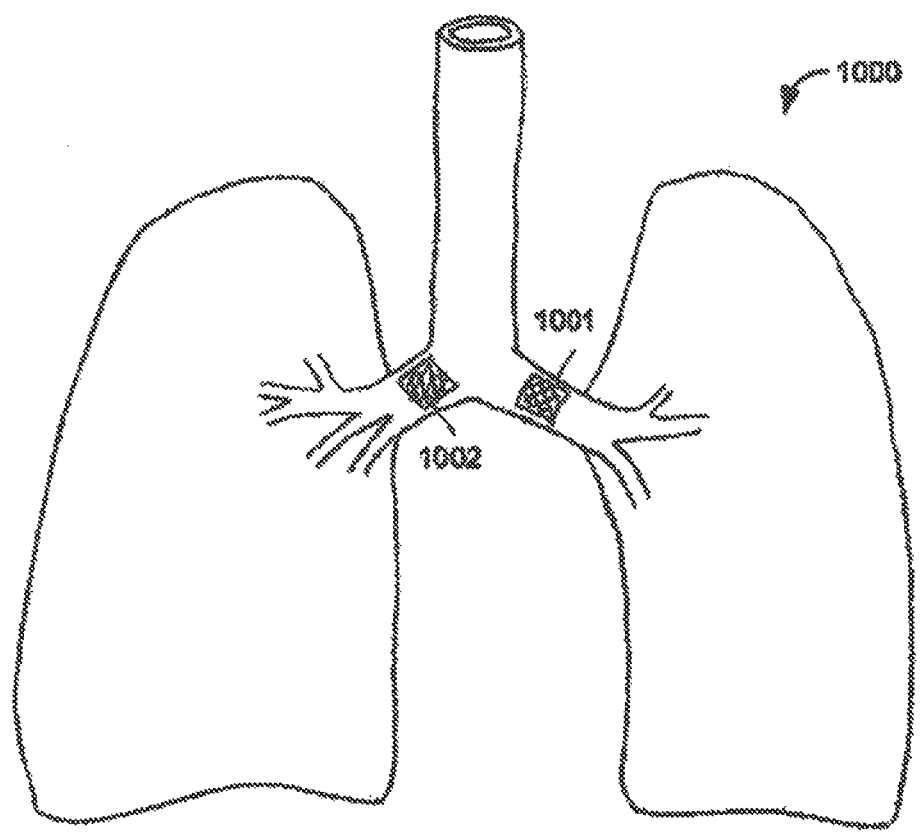

FIG. 10 illustrates generally an example of a system 1000 including first and second patch electrodes 1001, 1002 coupled to the left and right bronchi.

Figure 11A:
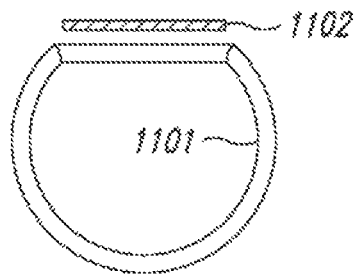
FIGS. 11A-11C illustrate generally example electrode configurations in, on, or surrounding at least a portion of a bronchus.
Figure 11B:
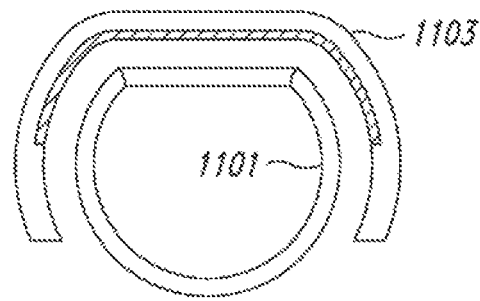
Figure 11C:
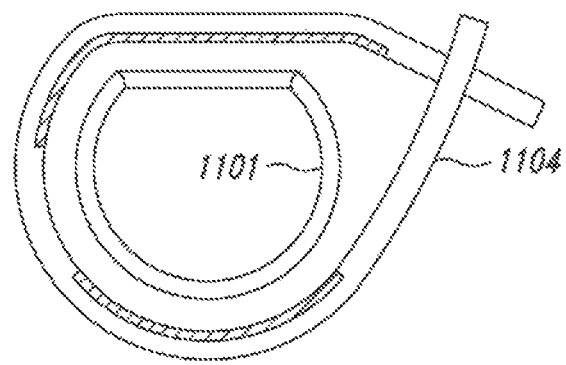

FIGS. 11A-11C illustrate generally example electrode configurations in, on, or surrounding at least a portion of a bronchus. FIG. 11A illustrates an example patch electrode configuration coupled to or near at least a portion of a dorsal side of a bronchus. FIG. 11B illustrates generally an example partial cuff electrode configuration coupled to or near the dorsal side of a bronchus. FIG. 11C illustrates generally an example full cuff electrode configuration coupled to, surrounding, or near at least a portion of a dorsal and ventral side of the bronchus. In other examples, other electrode configurations can be used. In an example, these, or other electrodes or electrode configurations, can be configured to be placed on the posterior (e.g., membranous aspect) of the bronchi.

Figure 12A:
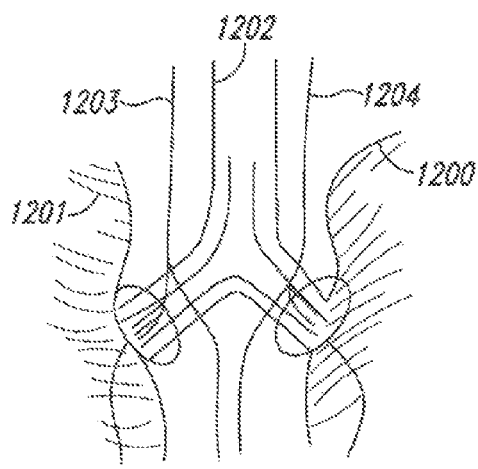
FIGS. 12A-12D illustrate generally an endo-bronchial electrode configuration and approach.

FIGS. 12A-12D illustrate generally an endo-bronchial electrode configuration and approach. FIG. 12A illustrates generally a dorsal view of a left lung 1200, a right lung 1201, a bronchi 1202, and pulmonary parasympathetic nerves 1203, 1204.

Figure 12B:
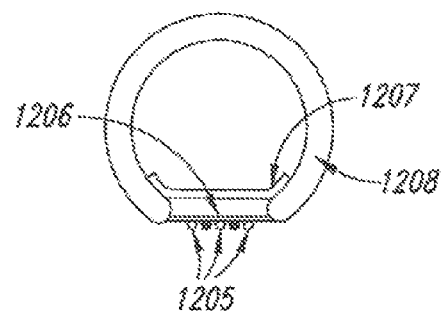

FIG. 12B illustrates generally an example of a wireless electrode 1206 and an antenna 1207 located in a trachea 1208 proximate pulmonary parasympathetic nerves 1205. In other examples, one or more wireless or other electrodes can be placed in the trachea 1208 or other location proximate the pulmonary parasympathetic sympathetic nerves 1205, or one or more other nerves.

Figure 12C:
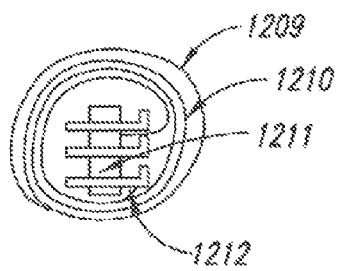

FIG. 12C illustrates generally an example of a silastic patch 1209, one or more electrodes 1212 (e.g., plunge or other electrodes), an embedded antenna 1210, and a control circuit 1211. In an example, the one or more electrodes 1212 can be sized or spaced be close to one or more dorsal pulmonary nerves, such as pulmonary parasympathetic nerves 1205.

Figure 12D:
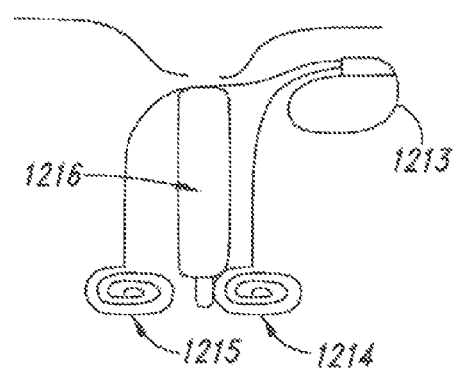

FIG. 12D illustrates generally an example of an implantable nerve stimulation pulse generator 1213 coupled (e.g., using one or more leads) to subcutaneously transmitting antennas 1214, 1215 on either side of a sternum 1216. In an example, the nerve stimulation pulse generator 1213 can be configured to deliver energy to one or more endo-bronchial electrode. In other examples, the endo-bronchial electrodes, such as the one or more electrodes 1212 can be configured to communicate with the nerve stimulation pulse generator 1213, or other implantable pulse generator, using the subcutaneously transmitting antennas 1214, 1215, or one or more other communication or telemetry devices.

Figure 13:
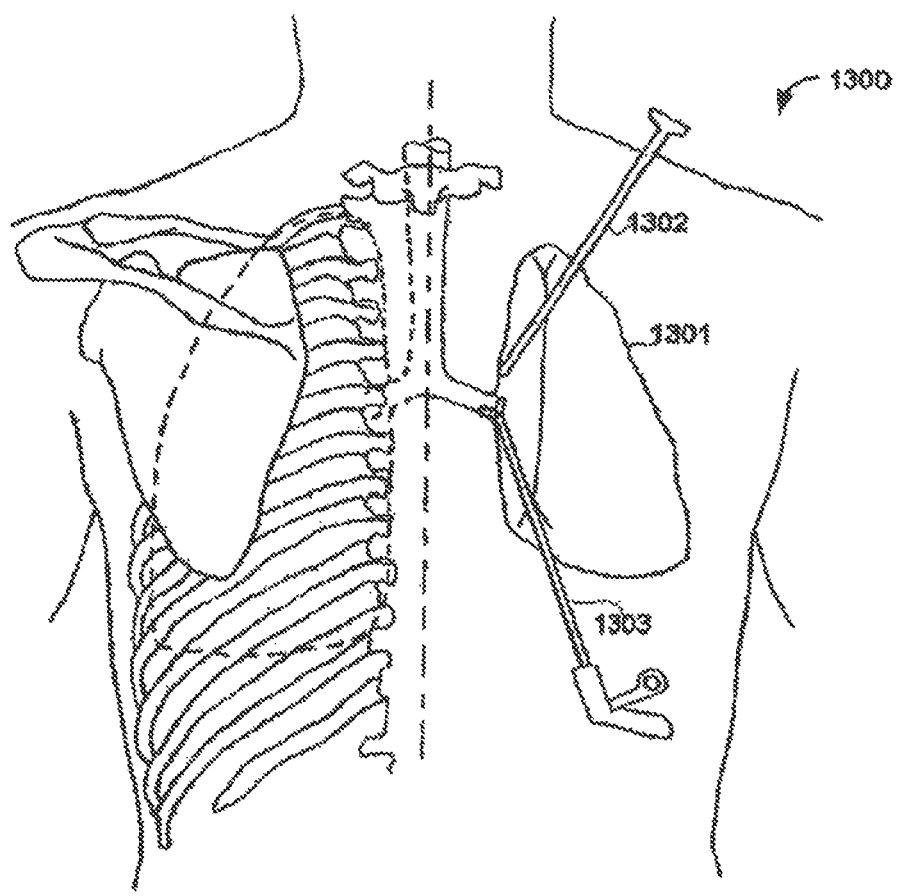
FIG. 13 illustrates generally a relationship between a bony structure and lungs, and an example of accessing the root of the main bronchi using two ports.

FIG. 13 illustrates generally a relationship between a bony structure and lungs, and an example of accessing the root of the main bronchi using two ports.

In an example, one or more ports can be placed between the ribs at any location between the shoulder blade and the spinal column, and from the second rib down to the tenth rib (typically at the fourth through eighth rib interspaces). In other examples, access can be gained lateral to the shoulder blade and along the anterior (i.e., ventral) aspect of the thorax.

In this example, a right lung 1301 is shown to be deflated and falling lateral and anterior within the thoracic cavity. In an example, the first port can be located approximately at the fourth rib interspace and the second port can be located approximately at the sixth rib interspace. Various instruments, such as a fiberscope 1302, a dissection tool 1303, etc., can be inserted through the first or the second port.

Other Examples

In an example, a system can include an implantable signal generator configured to generate a blocking signal to be delivered to at least a portion of a bronchus of a subject. In an example, the blocking signal can be configured to inhibit nerve traffic both to and from a lung of the subject, to relieve bronchial smooth muscle contraction, and to inhibit cough and mucus production.

In certain examples, the system can include a mucus sensor, configured to detect an indication of mucus buildup in at least a portion of the bronchus. Further, the system can include a processor, communicatively coupled to the implantable signal generator and the mucus sensor, the processor configured to control delivery of the blocking signal, and to stop delivery of the blocking signal, using the indication of mucus buildup, to allow mucus clearance.

In this example, the blocking signal can be provided for sustained periods of time, or according to one or more therapy algorithms (e.g., having a duty cycle, a scheduled "on" and "off" time, etc.). If the indication of mucus buildup is received, the therapy algorithm can be interrupted to provide for a period of no blocking signal, configured to allow cough and clear built up mucus.

Further, in certain examples, the blocking signal can be provided to inhibit mucus production.

Some Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like. Further, in certain examples, a processor configured to perform a function or operation can include one or more processors, each configured to perform at least a portion of the function or operation.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of treating a patient with a signal generator and an electrode operatively coupled to the signal generator, the method comprising:
    delivering energy from the signal generator via the electrode to nerve tissue located along an airway in the patient so as to have an effect on the patient, the effect being selected from the group consisting of: impeding nerve signal traffic to and/or from a lung of the patient, relieving bronchial smooth muscle contraction, facilitating nerve signal traffic to and/or from the lung of the patient to provide pulmonary maintenance, and combinations thereof.

2. The method of claim 1, wherein the electrode is configured to be positioned proximate the bronchus or trachea so as to at least partially extend circumferentially about at least a portion of an inner or outer surface of the bronchus or trachea.

3. The method of claim 1, wherein the signal generator is programmed to inhibit adaptation of a nervous system of the patient to the delivery of energy to the nerve tissue.

4. The method of claim 1, wherein the energy generated by the signal generator comprises a blocking signal.

5. The method of claim 1, wherein the signal generator is configured to deliver the blocking signal at a frequency between 10 and 5000 Hertz, at an amplitude between 0.1 and 10 milliamps, and with a pulse width between 50 microseconds and 2 milliseconds.

6. The method of claim 1, wherein delivering energy from the signal generator via the electrode to the nerve tissue is configured to damage the nerve tissue, the method further comprising:
inhibiting re-innervation of the nerve tissue.

7. The method of claim 6, wherein inhibiting re-innervation of the nerve tissue includes implanting an active stimulation system that substantially inhibits nerve signals at the airway to maintain the effect on the patient.

8. The method of claim 1, wherein the electrode is an implantable electrode configured to be positioned proximate the nerve tissue located along the airway in the patient.

9. The method of claim 1, wherein delivering energy from the signal generator via the electrode to the nerve tissue is based on an indication of a decrease in bronchial diameter.

10. The method of claim 9, wherein the indication is provided by a sensor.

11. The method of claim 1, wherein delivering energy from the signal generator via the electrode to the nerve tissue is based on input received from another device.

12. The method of claim 11, wherein the other device comprises a programmer.

13. The method of claim 11, wherein the other device is operable by a clinician.

14. The method of claim 11, wherein the other device is operable by the patient.

15. A system for treating a patient with an electrode operatively coupled to a signal generator, the system comprising:
an electrode operatively coupled to the patient;
a signal generator operatively coupled to the electrode;
one or more sensors configured to detect at least one condition of an airway;
wherein the signal generator is configured to deliver energy via the electrode to the patient based on the at least one condition of the airway so as to have an effect on the patient, the effect being selected from the group consisting of: impeding nerve signal traffic to and/or from a lung of the patient, relieving bronchial smooth muscle contraction, facilitating nerve signal traffic to and/or from the lung of the patient to provide pulmonary maintenance, and combinations thereof.

16. The system of claim 15, wherein the one or more sensors are external to the patient.

17. The system of claim 15, wherein the one or more sensors are implantable in the patient.

18. The system of claim 15, wherein the one or more sensors are selected from the group consisting of cough sensors, mucous sensors, and combinations thereof.

19. The system of claim 18, wherein the one or more sensors comprise a mucous sensor configured to detect mucus or other matter, to detect a building or accumulation of mucus or other matter in the lungs or bronchi, or combinations thereof.

20. The system of claim 19, wherein the mucus sensor comprises an impedance sensor.

21. The system of claim 15, wherein the electrode is an implantable electrode configured to be positioned proximate nerve tissue located along the airway in the patient.

* * * * *

UNITED STATES PATENT AND TRADEMARK OFFICE
CERTIFICATE OF CORRECTION

PATENT NO. : 9,867,986 B2  
APPLICATION NO. : 15/401825  
DATED : January 16, 2018  
INVENTOR(S) : Hlavka et al.

Page 1 of 1

It is certified that error appears in the above-identified patent and that said Letters Patent is hereby corrected as shown below:

On the Title Page

Add Item (73):  
Assignee: Nuvaira, Inc., Plymouth, MN (US)

Signed and Sealed this  
Twenty-seventh Day of March, 2018

Andrei Iancu  
*Director of the United States Patent and Trademark Office*